United States Patent
Park et al.

(10) Patent No.: US 9,283,386 B2
(45) Date of Patent: Mar. 15, 2016

(54) NEURAL ELEMENT COMPRISING NANOWIRES AND SUPPORT LAYER

(71) Applicant: Industry-Academic Cooperation Foundation, Yonsei University, Seoul (KR)

(72) Inventors: Seung Han Park, Seoul (KR); Jong Ill Hong, Seoul (KR); Jae Young Choi, Seoul (KR); Heon Jin Choi, Seoul (KR); Jae Chul Pyun, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 0 days.

(21) Appl. No.: 14/348,255

(22) PCT Filed: Jan. 25, 2013

(86) PCT No.: PCT/KR2013/000598
§ 371 (c)(1),
(2) Date: Mar. 28, 2014

(87) PCT Pub. No.: WO2013/111985
PCT Pub. Date: Aug. 1, 2013

(65) Prior Publication Data
US 2014/0228738 A1  Aug. 14, 2014

(30) Foreign Application Priority Data
Jan. 27, 2012 (KR) .................. 10-2012-0008306

(51) Int. Cl.
*A61N 1/30* (2006.01)
*A61N 1/36* (2006.01)
(Continued)

(52) U.S. Cl.
CPC .......... *A61N 1/36067* (2013.01); *A61B 5/0031* (2013.01); *A61B 5/4041* (2013.01);
(Continued)

(58) Field of Classification Search
CPC .. A61B 5/04001; A61B 5/0478; A61B 5/685; A61B 2018/1425; A61B 2562/028; A61B 2562/0285; A61B 5/0006; A61B 5/6848; A61L 31/16; A61N 1/05; A61N 1/0529; A61N 1/04; A61N 1/0456; A61N 1/0464; A61N 1/205; A61N 1/326
USPC .......................................................... 604/20
See application file for complete search history.

(56) References Cited

U.S. PATENT DOCUMENTS

2002/0117659 A1  8/2002  Lieber et al.
2004/0133118 A1  7/2004  Llinas
(Continued)

FOREIGN PATENT DOCUMENTS

KR    20090041309 A    4/2009
KR    20090041658 A    4/2009
(Continued)

OTHER PUBLICATIONS

Branner et al. "Long-Term Stimulation and Recording With a Penetrating Microelectrode Array in Cat Sciatic Nerve." *IEEE Trans. Biomed. Eng.* 51.1(2004):146-157.
(Continued)

*Primary Examiner* — Jason Flick
(74) *Attorney, Agent, or Firm* — Mintz Levin Cohn Ferris Glovsky and Popeo, P.C.; Fred C. Hernandez; Linyu L. Mitra

(57) ABSTRACT

Provided is a neural device including a nanowire and a support layer. Further, provided is a neural device including: a substrate, at least one nanowire which is fixed on the substrate at a lengthwise end thereof to extend vertically and inserted into nerves to obtain electrical signals from nerve fibers or apply electrical signals to the nerve fibers; and a support layer which is formed on the substrate and which surrounds and supports at least one portion of the nanowire.

22 Claims, 15 Drawing Sheets

(51) Int. Cl.
   *A61N 1/05*   (2006.01)
   *A61B 5/00*   (2006.01)
   *A61L 31/16*  (2006.01)
(52) U.S. Cl.
   CPC ............... *A61B5/6877* (2013.01); *A61L 31/16* (2013.01); *A61N 1/0529* (2013.01); *A61N 1/0551* (2013.01); *A61N 1/36125* (2013.01)

(56) References Cited

U.S. PATENT DOCUMENTS

2006/0287660 A1* 12/2006 Syed et al. .................... 606/152
2010/0305657 A1* 12/2010 Park et al. ...................... 607/45

FOREIGN PATENT DOCUMENTS

KR   100943415   B1   2/2010
KR   20110124575  A   11/2011

OTHER PUBLICATIONS

He et al. "Si Nanowire Bridges in Microtrenches: Integration of Growth into Device Fabrication." *Adv. Mater.* 17(2005):2098-2102.
Ramachandran et al. "Design, in vitro and in vivo Assessment of a Multi-Channel Sieve Electrode with Integrated Multiplexer." *J. Neural Eng.* 3(2006):114-124.
Zeck et al. "Noninvasive Neuroelectronic Interfacing with Synaptically Connected Snail Neurons Immobilized on a Semiconductor Chip." *PNAS.* 98.18(2001):10457-01462.

* cited by examiner

NEURAL ELEMENT COMPRISING NANOWIRES AND SUPPORT LAYER

CROSS-REFERENCE TO RELATED APPLICATIONS

This application is a national stage application, filed under 35 U.S.C. §371, of International Application No. PCT/KR2013/000598, filed Jan. 25, 2013, which claims priority to and the benefit of Korean Patent Application No. 10-2012-0008306, filed Jan. 27, 2012, the contents of each of which are incorporated herein by reference in their entireties.

TECHNICAL FIELD

The present invention relates to an intelligent neural device including a nanowire which transmits and receives an electrical signal, and more specifically a neural device having improved physical properties such as durability due to a nanowire surrounded and supported by insulating materials or the like.

BACKGROUND ART

In anatomy, a nerve is a fine long structure capable of being visibly observed, and histologically, is composed of a plurality of nerve bundles. Meanwhile, a nerve bundle is a collection of a plurality of nerve fibers. A nerve fiber denotes a portion of an axon in a nerve cell, and is known as a nerve fiber because the axon has a fine long fibrous shape. Various terms such as axon are used to refer to a nerve fiber.

All nerve fibers are surrounded by endoneurium, a soft connective tissue, nerve bundles are surrounded by perineurium, and nerves, which are bundles of nerve bundles, are surrounded by epineurium. All these membranes are provided to protect nerves, and only the epineurium is distinguishable with the naked eye.

In general, muscles of a human body operate according to electrical stimuli provided from nerves. Accordingly, when abnormality of facial muscles occurs, treatment of nerves connected to the corresponding muscles may be needed When abnormality of facial nerves or laryngeal nerves occurs, treatments such as drugs, surgery, or the like are performed. In this case, patients receive local massages of corresponding parts in order to stimulate damaged muscles by stimuli to peripheral nerves during recovery of damaged nerves, preventing atrophy of the muscles.

That is, when stimuli to the muscles are obstructed due to surgery, or the like of patients with facial or laryngeal nerve paralytics, since the corresponding muscles may be damaged, causing permanent muscle damage or paralysis, methods of massaging muscles related to the corresponding nerve system or providing electrical stimuli from the outside, or the like have been proposed.

Meanwhile, a conventional device configured to be inserted into a human body to provide a physical stimulus or obtain information of a certain numerical value in the human body has been proposed, and conventional devices are described as follows, which include electrodes providing or detecting electrical stimuli for nerves.

First, a device detecting electric signals of nerves based on a metal-oxide-semiconductor field effect transistor (MOSFET) has been conventionally proposed. This related art is a technique monitoring change of membrane capacitance depending on exterior stimuli using gatings of a MOSFET device, and is a technique of simultaneously monitoring various neural responses. This related art has been applied to a method of detecting nerve signals by fixing positions of snail neurons around a P-MOSFET with picket fences made of polyimide and culturing them with limited mobility (Zeck et. al., Noninvasive neuroelectric interfacing with synaptically connected snail neurons immobilized on a semiconductor chip, Proc Nat Acad Sci 2001; 98).

Second, a technique for detecting electric stimuli of brain stems or nerve fibers has been proposed. Since 2000, the Normann group at University of Utah (USA) and Cyberkinetics have been conducting research on measuring electric signals and stimulating nerves by directly inserting multiple electrodes in nerves and brains (Normann et. al., Long-Term Stimulation and Recording With a Penetrating Microelectrode Array in Cat Sciatic Nerve, IEEE Transactions on Biomedical Engineering, VOL. 51, NO. 1, JANUARY 2004).

Third, a technique of inserting sieve electrodes in nerve fibers has been proposed. Through joint research of Fraunhofer-IBMT (Germany), IMTEK (Germany) and others, regeneration of nerves has been studied and recording of nerve signals has been attempted by inserting sieve electrodes to be curved into nerve fibers and applying electric stimuli thereto (Anup et.al., Design, in vitro and in vivo assessment of a multi-channel sieve electrode with integrated multiplexer, J. Neural Eng. 3 (2006) 114-24) A total diameter of the sieve is the same as that of a rat sciatic nerve (1.5 mm), and 571 holes having a diameter of 40 µm are disposed therein at 70 µm intervals. In addition, ring-shaped electrodes cover 27 holes and their area is 2200 $\mu m^2$.

In the case of the first related art described above, there is a problem that noise of the MOSFET device is high and thus only a tendency of electric signals can be measured. Further, in the case of the second related art described above, there is a problem that brain stems or nerve cells are killed when electrodes are inserted. Further, when the sieve electrodes of third related art described above are inserted, cross-talk between the electrodes is generated, and thus there is a problem that the electric signals are not accurately detected.

DISCLOSURE

Technical Problem

The present invention is directed to providing a neural device capable of solving a damaged muscle problem by continuously providing electrical stimuli to a nerve system without killing nerve fibers and obtaining electrical signals therefrom.

The present invention is directed to providing a neural device having improved physical properties such as durability due to a nanowire surrounded and supported by insulating materials.

The present invention is directed to providing a neural device which is capable of transmitting and receiving electrical signals or electrical stimuli by electrically connecting a plurality of processing modules to each other even when a portion of a nerve is cut.

The present invention is directed to providing a patch type neural device using nanowires, which is capable of detecting or stimulating nerve signals on a nerve system having wide area such as cerebral cortex by attaching nanowire tips to a flexible substrate.

The present invention is directed to providing a neural device which is capable of selecting a specific nerve bundle to stimulate or detect signals using a cuff which includes a nanowire-based probe in the inner side and may be smaller than an existing cuff.

The present invention is directed to providing a neural device in which nanowires are disposed in a different direction from a processing module and thereby are not disturbed when being inserted into nerves.

The present invention is directed to providing a neural device in which data such as electrical signals obtained by an intelligent neural device including nanowires transmitting and receiving electrical signals is transmitted to an external communication module or data processed by the external communication module is transmitted to an internal neural device again.

Technical Solution

One aspect of the present invention provides a neural device including a substrate, at least one nanowire which is fixed on the substrate at a lengthwise end thereof and inserted into nerves to obtain electrical signals from nerve fibers or apply electrical signals to the nerve fibers; and a support layer which is formed on the substrate and which surrounds and supports at least one portion of the nanowire.

In the invention, the support layer may include at least one material selected from the group consisting of an insulating material, a biocompatible material, and a biodegradable material, and may also include a drug.

Another aspect of the present invention provides a neural device including a substrate having a through hole; an electrode part including at least one unit electrode part including a plurality of nanowires, which are fixed on the substrate at a lengthwise end thereof, and inserted into nerves to obtain electrical signals from nerve fibers or apply electrical signals to nerve fibers; a support layer which is formed on the substrate and which surrounds and supports at least one portion of the nanowire; and a processing module which is electrically connected to each of the unit electrode parts and controls electrical signals obtained from nerve fibers or electrical signals applied to the nerve fibers by the unit electrode part.

In the present invention, the processing module may include an internal communication module to transmit and receive data with an external communication module installed externally. In this case, the internal communication module and the external communication module may transmit and receive data by radio frequency (RF) or a wire, and the data may include electrical signals obtained from nerve fibers or electrical stimuli applied to the nerve fibers.

Still another aspect of the present invention provides a neural device including a substrate, and a plurality of nanowire modules including at least one nanowire which is fixed on the substrate at a lengthwise end thereof, and inserted into nerves to obtain electrical signals from nerve fibers or apply electrical signals to the nerve fibers; a support layer which is formed on the substrate and which surrounds and supports at least one portion of the nanowire; and a processing module which is electrically connected to the plurality of nanowire modules and transmits and receives electrical signals or electrical stimuli between nanowire modules selected from the plurality of nanowire modules.

According to the present invention, the processing module may process electrical signals obtained from a nanowire module selected from the plurality of nanowire modules, and apply electrical stimuli to another nanowire module.

According to the present invention, the substrate may be a patch type flexible substrate so as to be attached to a nerve system having wide area. The flexible substrate is advantageous when it is attached to a nerve system including a curved surface. Examples of the flexible substrate may include polyimide (PI), polydimethylsiloxane (PDMS), polyethylene (PE) polyethylene terephthalate (PET), Gore-tex (expanded polytetrafluoroethylene), or the like. In particular, polyimide is preferable in view of easy manufacture of a circuit or the like.

According to the present invention, a plurality of nanowires are collected to form a plurality of nanowire modules, which may be disposed in a lattice form. Disposition of nanowire modules is not limited to a lattice form, but the lattice form is considered advantageous in terms of preparation of a seed layer for generating nanowires, manufacture of a circuit, manufacture of a mask, and an easy practical process.

According to the present invention, a hole is formed in the substrate, and the hole provides another additional function, for example, a passage capable of regenerating a damaged nerve. In this case, electrical stimuli and nerve signals may be detected in the inner surface of the hole during generation of the nerve. The hole may be formed in various forms, and for example, disposed in a lattice form similarly to a nanowire module.

Yet another aspect of the present invention provides a neural device including a cuff formed in a hollow cylindrical form and having an open part in which a portion of a cylindrical periphery is cut; a plurality of nanowire modules including at least one nanowire which is fixed on the inner side of the cuff at a lengthwise end thereof and which is inserted into nerves to obtain electrical signals from nerve fibers or apply electrical signals to nerve fibers; a support layer which is formed on the inner side of the cuff and surrounds and supports at least one portion of the nanowire; and a processing module which is electrically connected to the plurality of nanowire modules and transmits and receives electrical signals or electrical stimuli between nanowire modules selected from the plurality of nanowire modules.

According to the present invention, the processing module may process electrical signals obtained from a nanowire module selected from the plurality of nanowire modules, and apply electrical stimuli to another nanowire module.

According to the present invention, a plurality of nanowires are arranged in one direction to form a nanowire module in a line form. In this case, the nanowire modules may be disposed so as to face each other in a cross form. The nerve fibers forming a nerve bundle transmit nerve signals so as to have different functions when signals by nerve stimuli are applied or detected in several portions as in a cross form, and the function of a cuff may be maximized through local stimulation or detection.

According to the present invention, a hole may be formed in the cuff, and the hole may have another additional function, for example, a passage for drug transfer from the outside, or the like. The type of the hole is not specifically limited, and may be formed in various forms.

According to the present invention, the nanowire module may be formed on a first surface of a substrate or a cuff, and the processing module may be formed on a second surface of the substrate or the cuff different from the first surface.

According to the present invention, an angle between a normal vector of the second surface and a normal vector of the first surface is 170° to 180°, and the nanowire module and the processing module may be connected to each other by a via hole.

According to the present invention, the via hole may be disposed outside of a complementary metal oxide semiconductor (CMOS) region of the substrate or the cuff.

Advantageous Effects

According to the present invention, the nanowires are surrounded and supported by insulating materials so that a physical property such as durability can be improved. When the support layer is formed of a biodegradable material, additional signals may be obtained in a biodegrading region. In addition, the support layer can be etched to be changed into a new material. In addition, the support layer may be supported with a drug such as an immunosuppressant.

In addition, while existing apparatuses for measuring nerve signals may kill nerve cells due to a large tip, in the present invention, nerve cells may be stimulated and detected without damage due to a tip of a nano level.

In addition, according to the present invention, electrical signals or electrical stimuli may be transmitted and received by electrically connecting a plurality of processing modules to each other even when a portion of a nerve is cut.

Further, while existing neural devices have to cut a nerve bundle, the patch type neural device according to an embodiment of the present invention may be used for a nerve system having a large area such as the brain without damage because it simply may cover the surface.

Further, while existing cuff apparatuses entirely stimulate a nerve bundle or detect signals therefrom, a nerve device having a cuff form according to an embodiment of the present invention selects a specific nerve bundle by changing a size thereof to stimulate or detect signals, and surrounds a nerve by a cuff structure, and therefore nerves are not damaged.

Further, according to the present invention, data such as electrical signals obtained by an intelligent neural device including nanowires is transmitted to an external communication module or data processed in the external communication module is transmitted to an internal neural device using radio frequency (RF) or a wire.

Further, in the neural device according to the present invention, nanowires are formed in a different direction from a processing module and thereby cannot be disturbed when being inserted into nerves.

MODES OF THE INVENTION

Hereinafter, the present invention will be described in detail with reference to the accompanying drawings.

The neural device according to the present invention includes materials of a nano size. Since the materials of a nano size have a higher ratio of surface area to volume according to a smaller size, an electrochemical reaction predominantly occurs on the surface, and hence it may be used for various sensors.

Particularly, one-dimensional nano materials such as a nano tube, a nano wire, and a nano bar are easily manipulated due to a high aspect ratio, and thus were among the first implemented nano devices.

The present invention proposes a nano wire-based neural device for obtaining electrical signals.

Figure 1:
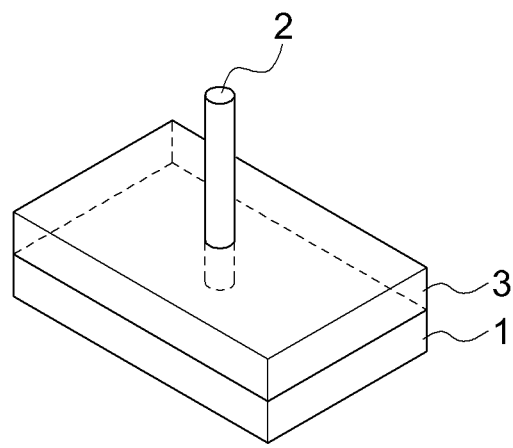
FIG. 1 is a perspective view of a neural device according to a first embodiment of the present invention.

FIG. 1 is a perspective view of a neural device according to a first embodiment of the present invention. The neural device includes a substrate 1, a nano wire 2, and a support layer 3.

The base substrate 1 may be formed of a metal, a plastic or a ceramic material.

The nanowire 2 is fixed on the substrate 1 at one lengthwise end thereof to extend vertically, and is inserted into a nerve to obtain electrical signals from nerve fibers or apply electrical signals to the nerve fibers. Specifically, the nanowire 2 is inserted into a nerve fiber in a nerve bundle to obtain electrical signals which occur along the surface of nerve cells in the nerve fiber or provide electrical stimuli to nerve cells in the nerve fiber.

Conventionally, when electrodes of a macro size are arranged and inserted into nerve fibers, the nerve fibers may be damaged and killed. Whereas, according to the present invention, since the nanowire 2 is used in order to obtain electrical signals and/or provide electric stimuli, damage to nerve fibers may be minimized.

Generally, since the nerve fiber has a diameter of several micrometers or more and the nanowire 2 has a diameter of tens to hundreds of nanometers (nm), there is no significant damage to the nerve fiber even when the nanowire 2 is inserted into a portion of the nerve fibers to provide electrical stimuli to nerve cells in the nerve fibers or obtain electrical signals.

The nanowire 2 may be inserted in a longitudinal direction or vertical direction of the nerve fiber. When the nanowire 2 is inserted in the longitudinal direction, a contact area between the nanowire 2 and an outer side of the nerve fiber may be easily maximized.

The support layer 3 may be formed so as to partially surround the nanowire 2 on the substrate 1, and may be formed by a method such as, for example, coating or deposition. Specifically, a method of forming the support layer 3 may include coating the substrate with a biocompatible polymer by irradiation using light with high energy such as electron beams or γ-rays, or grafting polymerization by plasma treatment. Further, the support layer 3 may be deposited by chemical vapor deposition (CVD), or physical vapor deposition (PVD) such as sputtering, electron-beam deposition, or thermal deposition.

The support layer 3 serves to improve durability of the neural device by supporting the nanowire 1.

The support layer 3 has a thickness of, for example, 1 to 99%, 10 to 90%, 20 to 80%, or 50 to 70%, based on the height of the nanowire 2.

The support layer 3 may include at least one selected from the group consisting of an insulating material, a biocompatible material, and a biodegradable material.

The support layer 3 may have insulating properties due to insulating materials contained therein, and is preferably formed of a biocompatible material in order to be inserted into a human body. For example, the support layer 3 may include a biocompatible thin or thick film stacked on a substrate of a metal and/or a resin. The biocompatible thin or thick film may be obtained by surface modification using an organic silane with at least one hydrophilic group such as an amine, a hydroxyl, or a carboxyl, and may include a biocompatible thin or thick film such as parylene with the hydrophilic functional group. Meanwhile, the biocompatible thin or thick film includes carbon, silicon, carbonsilicon, silicon oxide, a silicon polymer, silcon nitride, alumina, apatite hydroxide, bioglass, tricalcium phosphate ceramics, a natural polymer such as chitosan, a polypeptide, a polysaccharide, or a polynucleotide, or a biocompatible material such as a biocompatible polymer. Further, examples of the biocompatible material include a hydrogel, collagen, silk, polyhydroxyethyl-methacrylate (polyHEMA), polyethylene glycol (PEG), polyurethane (PU), teflon, polymethyl methacrylate (PMMA), or polyetheretherketone (PEEK).

The support layer 3 may be also formed of a biodegradable material, and the material includes a copolymer or homopolymer of lactic acid or glycolic acid; a polymer including, as a component, a carbohydrate-derived monomer such as a glucose derivative; a biodegradable hydrogel such as alginic acid; or a natural polymer such as a polypeptide, a saccharide, or a polynucleotide. Examples of the biodegradable polymer include polylactide (PLA), polyglicolide (PGA), polylactide-co-glicolide (PLGA), or poly ε-caprolactone (PCL), polydioxanone (PDO), or the like.

When the support layer 3 is formed of a biodegradable material, additional signals may be obtained in a biodegrading region.

The support layer 3 may be etched, so that a new region of the nanowire may be exposed. For example, when a portion of the nanowire is physically damaged, the support layer 3 may be partially etched to expose an intact portion of the surrounded nanowire. If necessary, when the exposed nanowire before etching is removed, it may be regenerated as a new device.

Etching may include plasma etching using $O_2$ or ozone, physical etching by accelerating ions such as Ar or Ga, or etching after converting the ions into plasma.

Further, the support layer 3 may be supported with a drug such as an immunosuppressant, a steroid, an antibiotic (Gentamycin or the like), a material promoting nerve regeneration (Brain-derived neurotrophic factor (BDNF) or the like), an anti-inflammatory agent (dexamethasone or the like), or a nerve transfer material (antagonist MK801 or the like). Therefore, the neural device may be used for treatment with a drug as well as fundamental functions such as obtaining and applying signals. For example, when a biodegradable material is mixed with a drug to prepare the support layer 3, the drug may be discharged according to decomposition of the biodegradable material.

If necessary, the support layer 3 may be formed of at least one layer. For example, the support layer 3 may include a first support layer, which is formed on the substrate, serving to insulate through an insulating material included therein, a second layer, which is formed on the first support layer, serving to support the nanowire with a biocompatible material included therein, and a third support layer, which is formed on the second support layer, serving to discharge a drug through a biodegradable material included therein.

Figure 2:
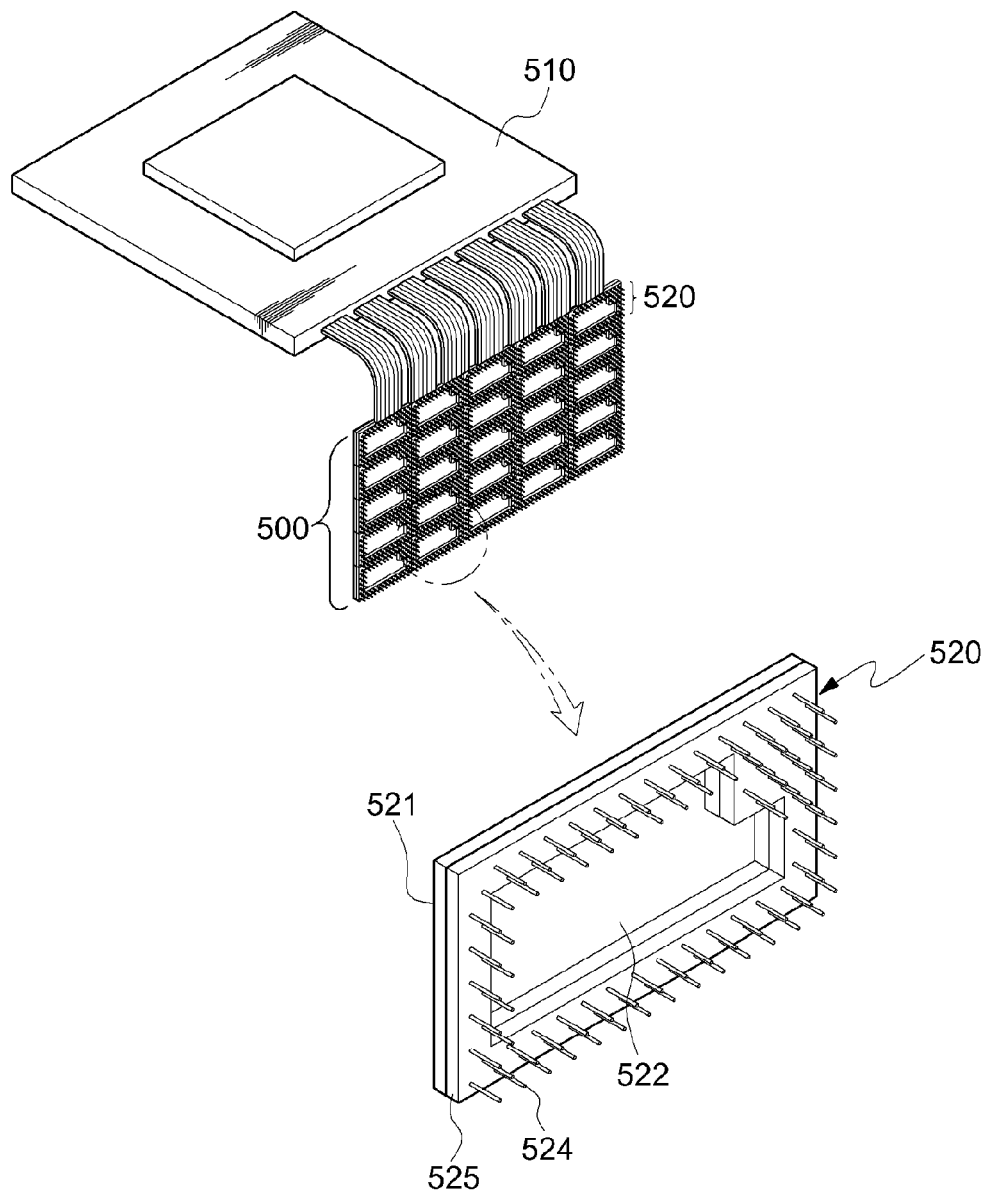
FIG. 2 is a perspective view of a neural device according to a second embodiment of the present invention.

FIG. 2 shows a neural device according to a second embodiment of the present invention.

Hereinafter, drawings in which a size of each member is enlarged or reduced for convenience in description are shown. Accordingly, the present invention is not limited to specific numerical values of the accompanying drawings.

The neural device according to the second embodiment of the present invention includes an electrode part 500. The electrode part 500 includes at least one unit electrode part 520. The unit electrode part 520 includes a base 521 with a through hole 522, a plurality of nanowires 524, which are fixed on any one surface of the base 521 at a lengthwise end thereof to vertically extend, and inserted into nerves, and a support layer 525 which supports the nanowire.

A plurality of nanowires 524 included in the unit electrode part 520 obtain electrical signals from nerve fibers included in a nerve and apply electrical stimuli to the nerve fibers. Further, the nanowires 524 may also be configured so as to either obtain electrical signals or apply electrical stimuli. Some of a plurality of nanowires 524 included in the unit electrode part 520 may apply electric stimuli to nerve fibers and others may obtain electrical signals from the nerve fibers. For example, the unit electrode part 520 may include either a plurality of nanowires 524 obtaining electric signals from nerve fibers or a plurality of nanowires applying electrical stimuli to the nerve fibers. Further, the unit electrode part 520 may include a plurality of nanowires 524 obtaining electric signals from nerve fibers, a plurality of nanowires applying electrical stimuli to the nerve fibers, and a nanowire 524 either obtaining electric signals from nerve fibers or applying electrical stimuli to the nerve fibers.

The neural device according to the second embodiment of the present invention includes a processing module 510, which is electrically connected to each unit electrode part 520, and controls electrical signals obtained from the nerve fibers or electrical signals applied to the nerve fibers by the unit electrode part 520.

The processing module 510 controls electrical signals obtained from nerve fibers or electrical signals applied to the nerve fibers. The processing module 510 is a device capable of being manufactured using a conventional device used in the aforementioned related art.

The electrode part 500 according to the second embodiment of the present invention provides electrical signals obtained from the nerve fibers to the processing module 510 and applies electrical stimuli to the nerve fibers according to control of the processing module 510. In the unit electrode part 520, the base may include a complementary metal oxide semiconductor (CMOS) device or a charge-coupled device (CCD) attached thereto, which is electrically connected to the nanowire 524 and detects change of current of a plurality of nanowires 524 electrically connected to each other. In other words, according to control of the processing module 510, the CMOS device or CCD device controls the current to apply electrical stimuli to the nanowire 524 or to transfer electrical signals obtained from change of current of the nanowire 524 to the processing module 510.

The neural device according to one example of FIG. 2 includes at least one unit electrode part 520 including a base 521 with a through hole 522, a plurality of nanowires 524, a support layer 525, and a processing module 510.

The base 521 of the unit electrode part 520 is manufactured in a planar shape or any of various 3D dimensional shapes, includes a through hole 522 formed at a central portion thereof, and is connected to the processing module 510. At least one through hole 522 is preferably formed in the base 521. The through hole 522 may have various cross-sections such as a circular shape, an oval shape, a polygonal shape, or the like, and preferably may have a size of tens of micrometers to tens of nanometers. For example, the base 521 may be manufactured in polygonal shape for which manufacture and mass production are simple, and each side may have a length of 25 μm or longer and 30 μm or shorter.

Figure 3:
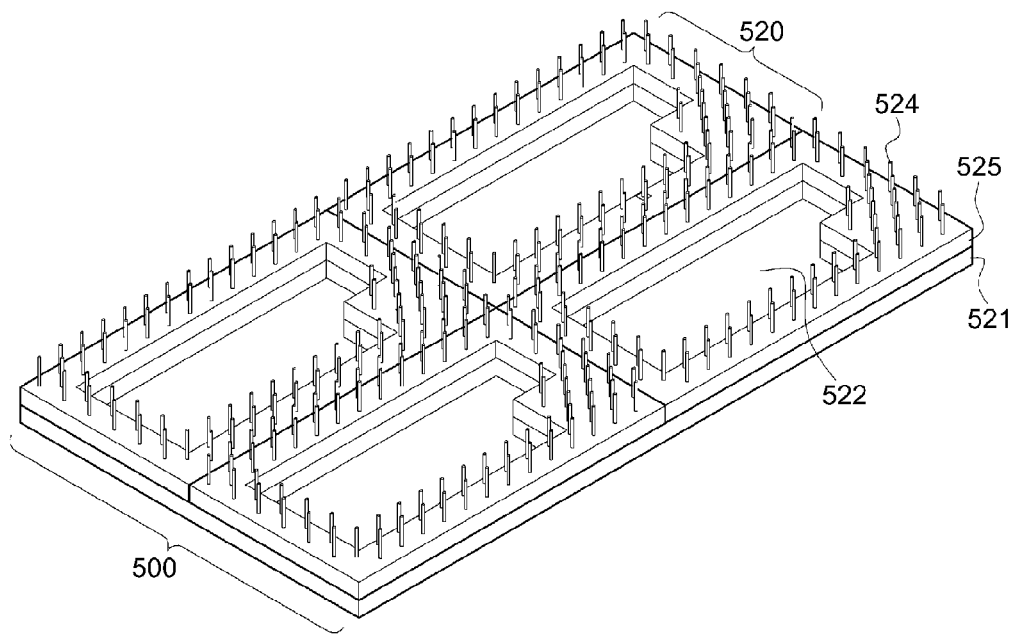
FIG. 3 shows disposition of a unit electrode part of a neural device according to a second embodiment of the present invention.

The unit electrode part 520 may be disposed in a plurality of rows and columns, and FIG. 3 is one example of a 2*2 array. Preferably, the unit electrode part 520 may be disposed in a 128*128 array. The base 521 includes the CMOS device or CCD device attached thereto, which is electrically connected to the nanowire 524 to apply or obtain electrical signals.

Figure 4:
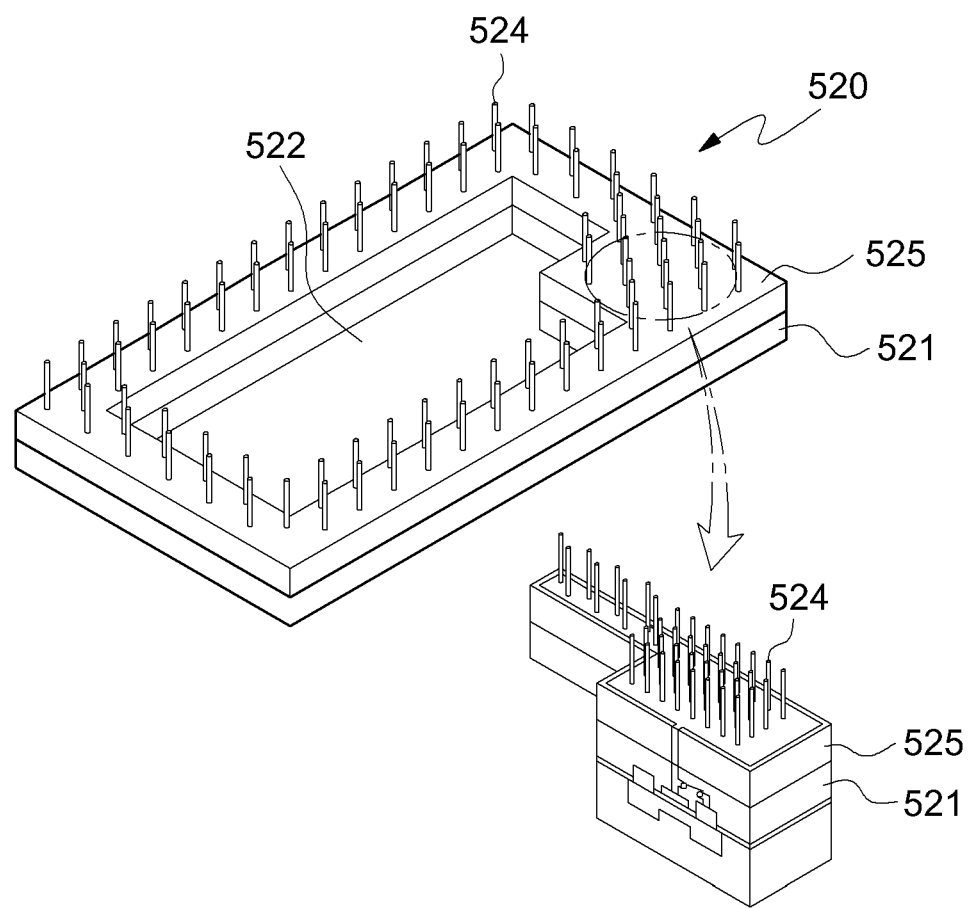
FIG. 4 shows a perspective view of the unit electrode part.

For example, FIG. 4 is a perspective view showing a CMOS in the base of the unit electrode part 520, and each unit electrode part 520 may include at least one CMOS device or CCD, in which a plurality of nanowires 524 are electrically connected to each other, and are electrically connected to the CMOS device or CCD.

Therefore, a plurality of unit electrode parts 520 constituting the electrode part 500 each include one CMOS device or CCD, in which electrical signals of a plurality of unit electrode parts 520 obtained from CMOS device or CCD may be processed by one processing module 510, and electrical stimuli may be applied through the CMOS device or CCD of each unit electrode part.

The base 521 includes the through hole 522 formed at the central portion thereof, through which a cross-section of a cut nerve fiber may be regenerated and recovered. A plurality of nanowires 524 may be disposed at predetermined intervals, and preferably formed in a bundle to support a load. Each of the nanowires 524 may be supported by a support part formed on any surface of the base 521.

The example of FIG. 2 relates to one example of the electrode part 500 connected to one side of the processing module 510. The electrode part 500 connected to the processing module 510 may obtain electrical signals from the nerve fibers, apply electric stimuli to the nerve fibers, or apply electrical stimuli and obtain electrical signals. On the other hand, the number of the electrode part 500 connected to one side of the processing module 510 is not limited.

For example, two electrodes may be connected to both sides of the processing module 510 facing each other. In this case, it is preferable that a first electrode part at one side of the processing module 510 obtain electrical signals from the nerve fibers and a second electrode part at the other side of the processing module 510 apply electrical stimuli to the nerve fibers. Therefore, the nanowires included in the first electrode part obtain electrical signals from the nerve fibers and the nanowires included in the second electrode part apply electric stimuli to the nerve fibers. In other words, a plurality of nanowires included in each of the electrode parts may either apply electrical stimuli or obtain electrical signals.

The neural device of FIG. 2 may be manufactured by various methods. In a case of synthesizing a nanowire using a catalyst, when a reactant is applied to a nano cluster, a nanowire is synthesized by nucleation and growth. In addition, the nanowire used in the present invention may also be formed by a method described in Si Nanowire Bridge in Trenaces: "Integration of Growth into Device Fabrication" Adv. Mater. 17, 2098, 2005.

A method for preparing the electrode 500 including the nanowires is as follows: The base 521 including the through-hole 522 may be formed on a wafer formed of various materials such as silicon, or the like through a photo mask and etching process.

When the base 521 including the through-hole 522 is formed, a catalyst is applied at a position at which the nanowire 524 generates on one surface of the base 521. For example, when one lengthwise end of the nanowire 524 is fixed along the edge of the base 521, a catalyst for generating the nanowire 524 is applied on the edge of the base. The catalyst may be positioned at an arbitrary portion of one surface of the base through a lithography process, or the like. The catalyst may be preferably selected according to a material of the nanowire 524 to be generated. For example, when a silicon nanowire 524 is generated, a Au catalyst may be used. When the catalyst is applied on the substrate, a reactant may be supplied to form the nanowire 524 through chemical vapor deposition (CVD).

The base 521 and the nanowire 524 may be formed of various materials. For example, the base and the nanowire may include silicon, gold, silver, iridium, iridium oxide, platinum, tin, nickel, chromium, rhenium, and copper, and various alloys of these metals, or a semiconductor device or a metal, which may be implemented as a nano device through a nano process.

Figure 5:
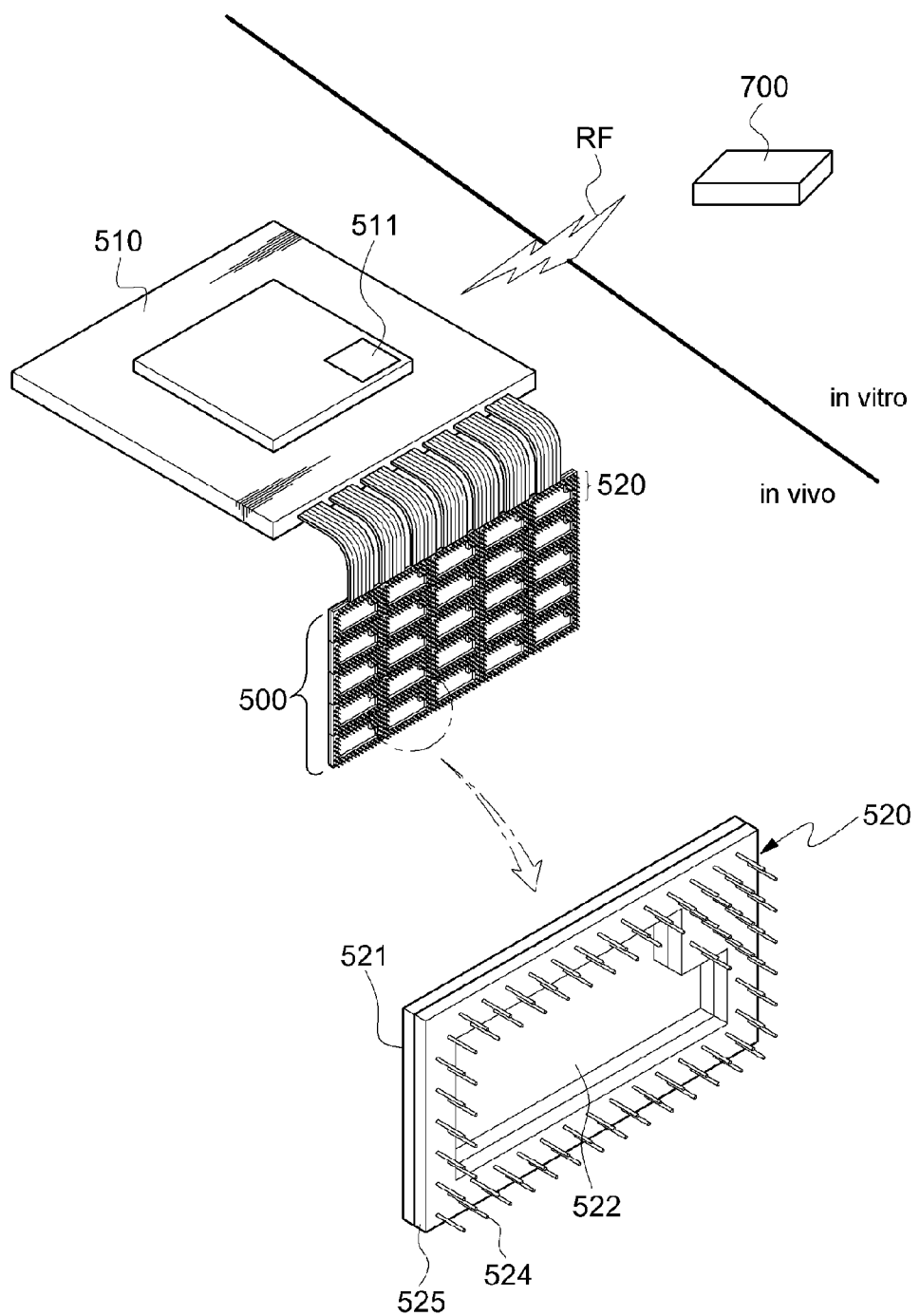
FIGS. 5 and 6 show a data communication method of a neural device according to a second embodiment of the present invention.
Figure 6:
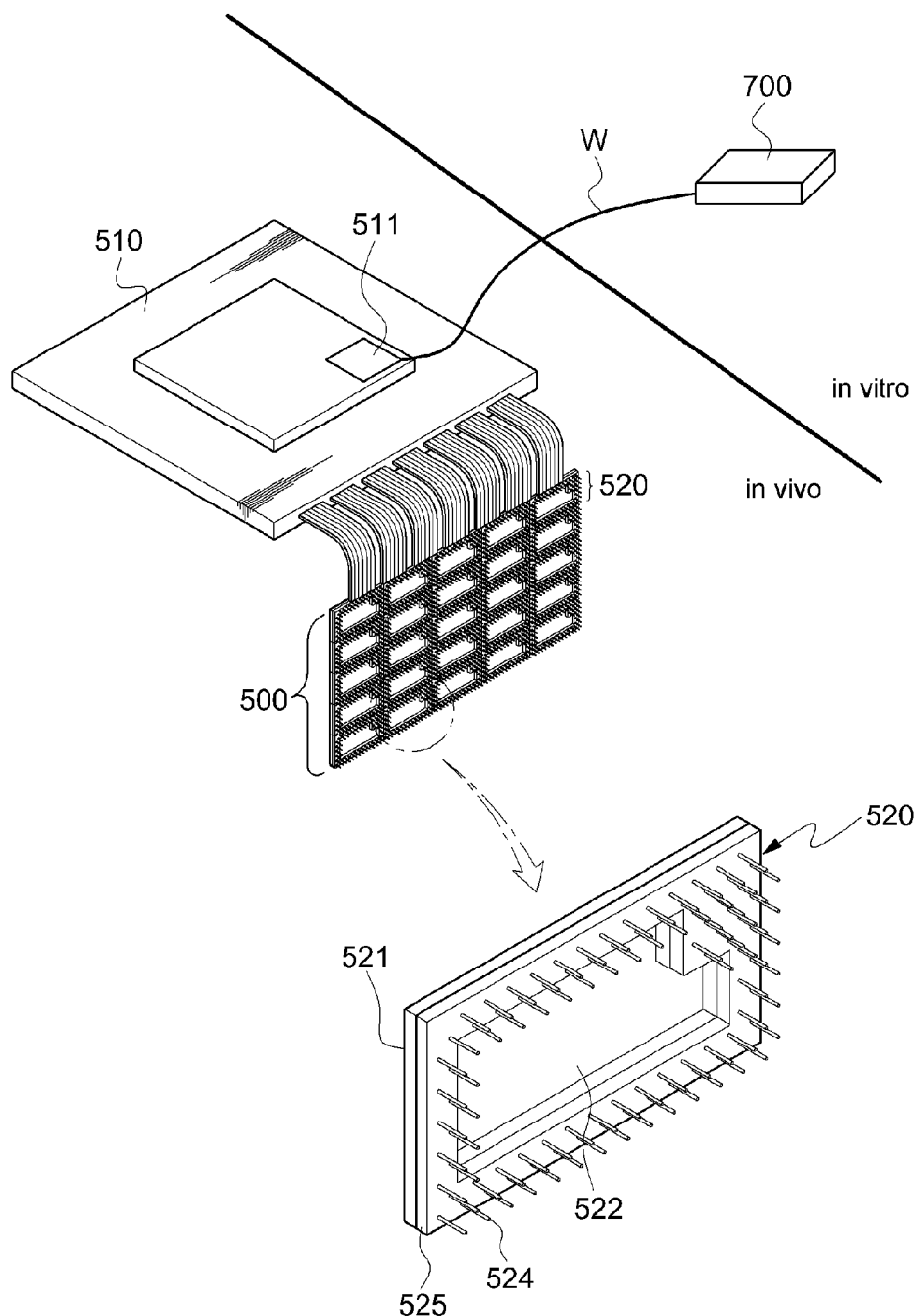

FIGS. 5 and 6 show a data communication method of a neural device according to the second embodiment of the present invention, and the electrode part 500 is inserted into nerve fibers and includes a base 521 with a through hole 522, nanowires 524, which are fixed on any one surface of the base 521 at a lengthwise end thereof to extend vertically, and a support layer 525 which supports the nanowire.

Subsequently, the electrode part 500 may transmit and receive data with nerve fibers. Herein, the data may include electrical signals obtained from a nerve fiber and electrical stimuli applied to the nerve fiber.

Subsequently, the processing module 510 which is electrically connected to the electrode part 500 controls transmission and reception of the electrode part 500.

Subsequently, the internal communication module 511 which is disposed in the processing module 510 transmits and receives data with the external communication module 700.

The internal communication module 511 and the external communication module 700 are general communication modules and may transmit and receive data using radio frequency (RF) as in FIG. 5 and a wire (W) as in FIG. 6.

Thus, data such as electrical signals obtained by an intelligent neural device including nanowires 524 is transmitted to the external communication module 700 or data processed in the external communication module 700 is transmitted to the internal neural device using radio frequency (RF) or a wire.

FIGS. 7 to 10 show a neural device according to a third embodiment of the present invention.

Figure 7:
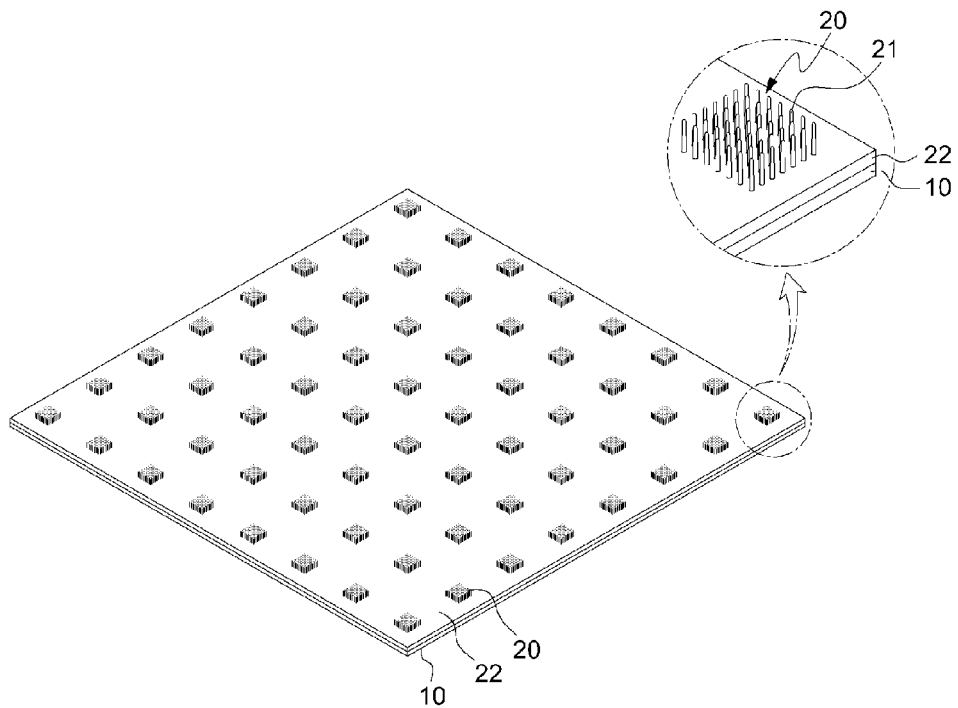
FIGS. 7 to 10 show a neural device according to a third embodiment of the present invention.

FIG. 7 is a perspective view of a patch type neural device including a nanowire module having a lattice form, and the neural device includes a substrate 10 having a wide area, a plurality of nanowire modules 20 formed on the substrate 10, and a support layer 22 formed on the substrate 10 so as to partially surround and support the nanowire 21.

The substrate 10 is a patch type attached to the surface of an organ of a human body, and preferably a flexible substrate so as to be attached to nerve system having a wide area.

The term "flexible" in the present specification refers to smooth, soft, and mild properties. Therefore, when a certain external force is applied, a flexible substrate may be easily bent or modified. Particularly, since the flexible substrate is advantageous when being attached to a nerve system including a curved surface, it is very suitable for the substrate 10 of the neural device according to the present invention.

Examples of the flexible substrate include PI, PDMS, PE, PET, or Gore-tex, and particularly, polyimide is preferable due to easy manufacture of a circuit.

The nanowire module 20 includes a plurality of nanowires as shown in a partially magnified view of FIG. 7. In other words, pluralities of nanowires 21 are collected to form nanowire modules 20.

The nanowire modules 20 may be disposed in a lattice form as shown in FIG. 7, but are not limited thereto and may be disposed in any of various forms. Disposition of the nanowire modules is considered advantageous in terms of preparation of a seed layer for generating nanowires, manufacture of a circuit, manufacture of a mask, and easy practical process.

The term "lattice" in the present specification refers to a structure, an article or type having a width and a height at predetermined intervals so as to form almost right angles, such as a checkerboard.

As shown in a partially magnified view of FIG. 7, the nanowire 21 is fixed on one surface of the substrate 10 at a lengthwise end thereof to extend vertically.

The term "vertical" in the present specification means that an angle between a straight line and a straight line, a straight line and a plane, or a plane and a plane is almost a right angle. For example, when the angle is within a range of 80 to 100°, it is considered almost a right angle. Further, even if a portion thereof is curved or bent, it is considered almost a straight line.

The nanowire 21 according to the embodiment may be inserted in a longitudinal direction or vertical direction of the nerve fiber, but the insertion direction is not limited.

As shown in the drawings, the support layer 22 may be formed so as to have the same area as the substrate 10, or formed only on the nanowire module 20.

Figure 8:
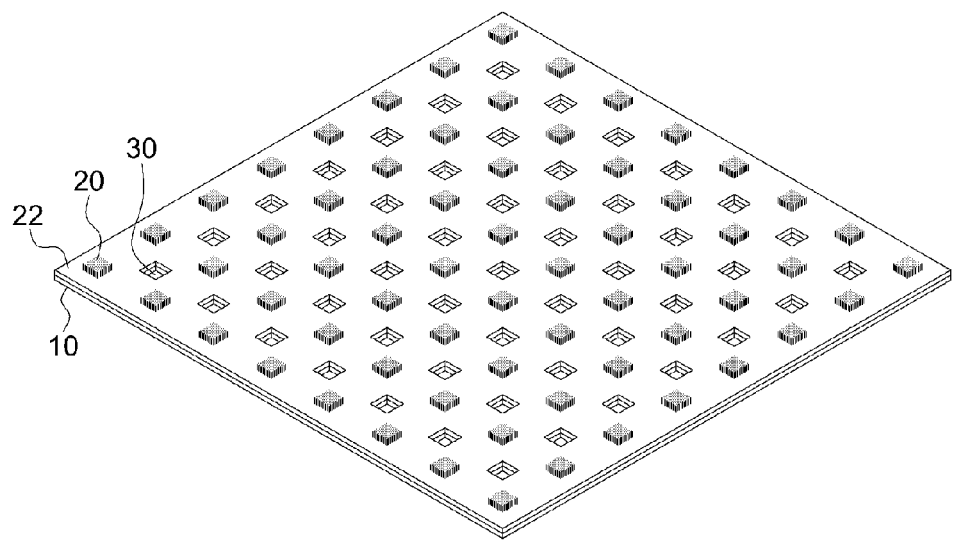

FIG. 8 is a perspective view of a neural device in which a hole is formed in the substrate for another function, and the neural device includes the substrate with a plurality of holes 30 unlike a neural device of FIG. 7.

The hole 30 provides another additional function, for example, a passage capable of regenerating a damaged nerve. In this case, electrical stimuli and nerve signals may be detected in the inner surface of the hole during generation of the nerve.

The hole 30 may be disposed in a lattice form as shown in FIG. 8, but is not limited thereto and may be disposed in any of various forms. However, the hole 30 is preferably disposed between the nanowire modules 20 not to be overlapped by or close to the nanowire modules 20.

Figure 9:
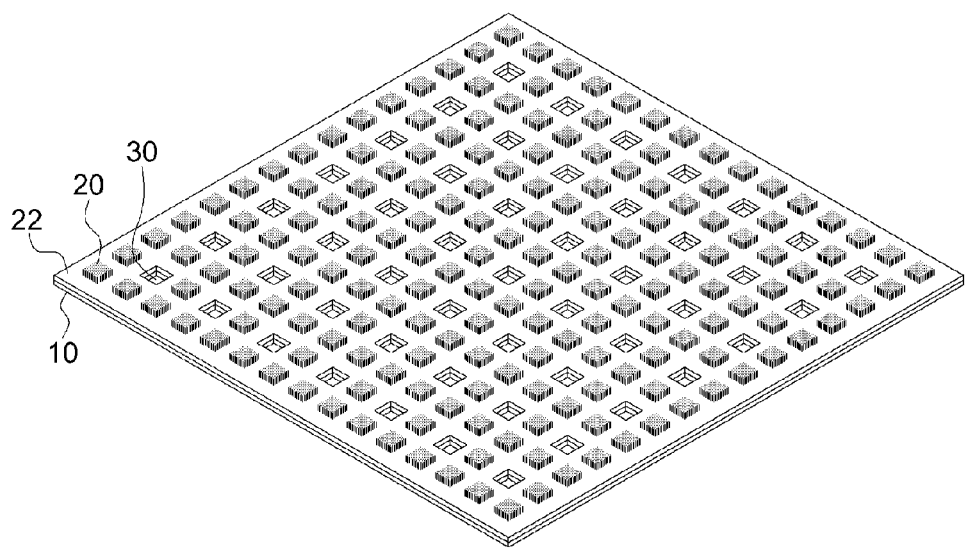

FIG. 9 is a perspective view of a neural device having an array of nanowires for insertion into nerves, and the neural device includes a plurality of nanowire modules 20 and holes 30, which are disposed in a lattice form similarly to the neural device of FIG. 8, but the nanowire modules are disposed more densely so as to entirely surround the hole 30 unlike the neural device of FIG. 8.

The nanowires in the structure of FIG. 9 have a higher density than those of the structure of FIG. 8 so that nerve stimuli may extend to a larger region, and a ratio of signal to noise may be increased as intensity of a detection signal increases.

Figure 10:
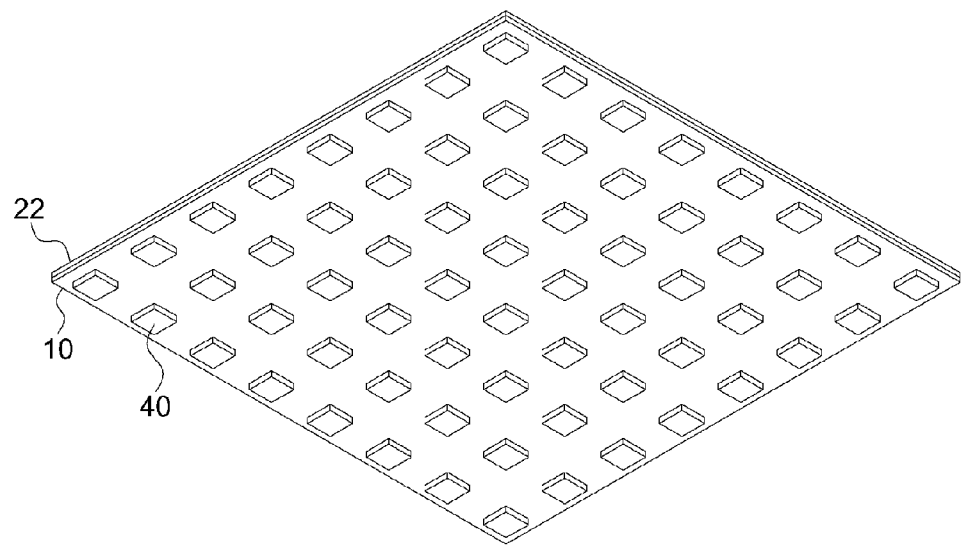

FIG. 10 is a perspective view of a neural device in which a processing module is attached to the lower side of a substrate according to the third embodiment of the present invention.

The processing module 40 serves to control nerve signals or electrical stimuli transmitted and received through the nanowire 21. The processing module 40 may include a CMOS device, or may be attached to a CMOS device.

The nanowire modules 20 are each electrically connected to the processing module 40. Further, a plurality of processing modules 40 are electrically connected to each other so that electrical signals or electrical stimuli may be transmitted and received, even when a portion of a nerve is cut.

While not shown in the drawings, the processing module 40 may include an internal communication module 511 which transmits and receives data with the external communication module 700.

Since the neural device according to the third embodiment of the present invention includes a tip having a size of a nano level, and simply covers the surface of a nerve system by a patch type, it may carry out stimulation and detection without damaging nerve cells and a nerve bundle need not be cut as in the related art. Further, the cuff structure may be used for body organs that were unable to be measured and detected with an existing cuff structure without damage, for example an organ such as the brain in which nerve cells are distributed in a wide area.

Figure 11:
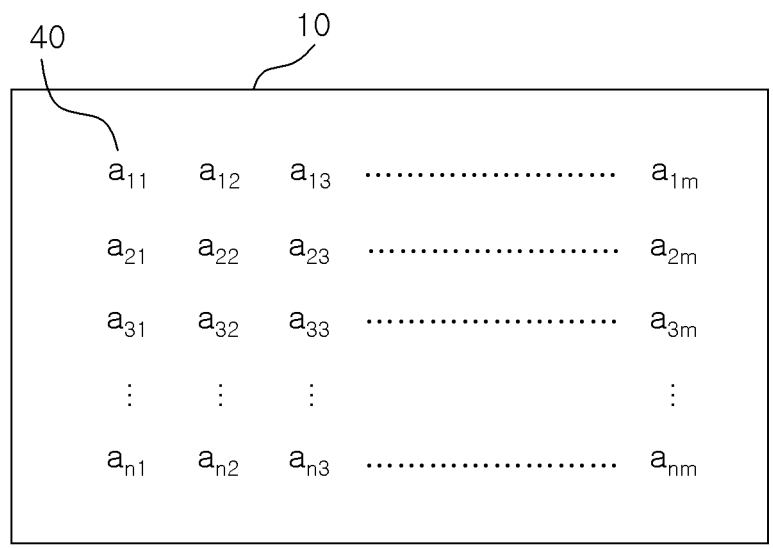
FIG. 11 is a schematic diagram showing a matrix of a processing module according to a third embodiment of the present invention.

FIG. 11 is a schematic diagram showing a matrix of a processing module according to the third embodiment of the present invention, in which a plurality of processing modules 40 are formed of, for example, a row of a11 to a1m and a column of a11 to an1 on the substrate 10.

Figure 12:
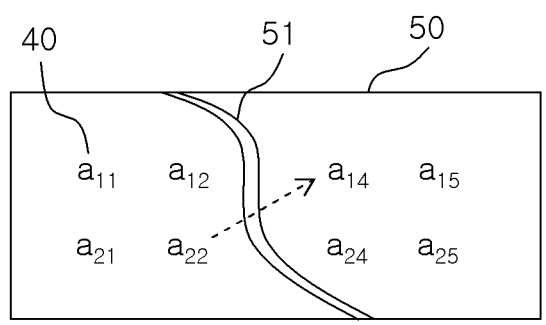
FIG. 12 is a schematic diagram showing one example of transmission and reception by a processing module at a position at which a nerve is cut according to a third embodiment of the present invention.

FIG. 12 is a schematic diagram showing an example of transmission and reception by a processing module at a position at which a nerve is cut according to the third embodiment of the present invention. In FIG. 12, even though a portion 51 of a nerve 50 is cut, for example a signal of a22 is transmitted to a14 across a position 51 at which the nerve 50 is cut in the processing module 40, and thus signals may be continuously processed without interruption.

FIGS. 13 to 16 show a neural device according to a fourth embodiment of the present invention.

Figure 13:
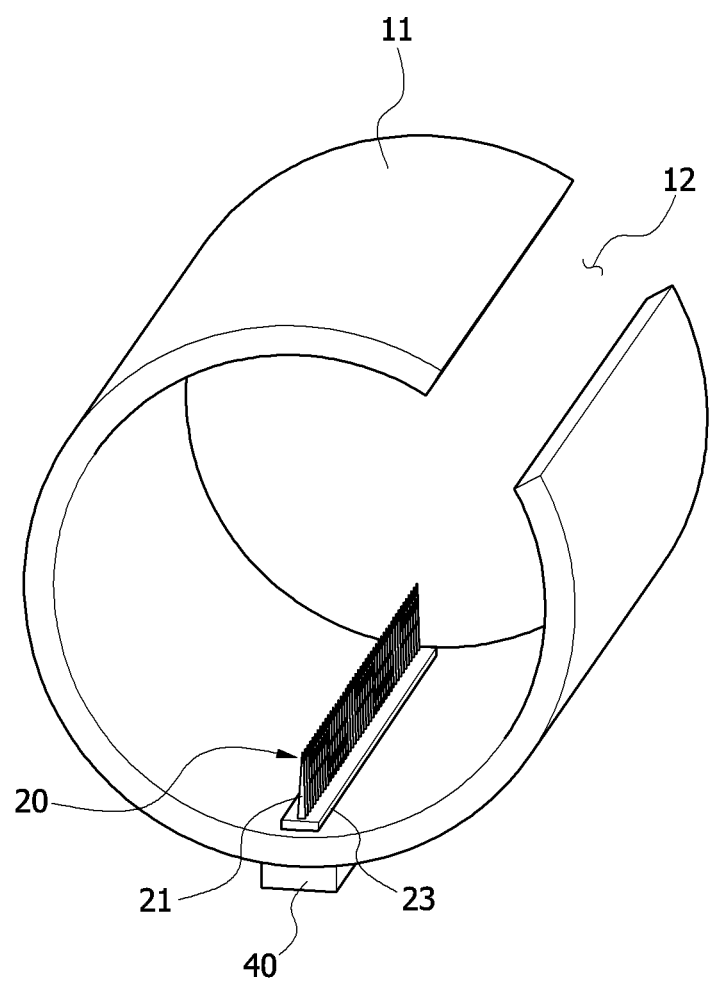
FIGS. 13 to 16 show a neural device according to a fourth embodiment of the present invention.

FIG. 13 is a perspective view of a neural device including one nanowire module, in which the neural device includes a cuff 11, a nanowire module 20, a support layer 23, and a processing module 40.

The cuff 11 is formed in a hollow cylindrical form, has an open part 12 in which a portion of a cylindrical periphery is cut, and nerves may be inserted thereinto through the open part 12.

A size of the open part 12 is not specifically limited, and if necessary, may be larger or smaller than that shown in the drawings. Further, the open part may be so small that both edges of the cuff are nearly in contact.

The cuff 11 according to the present invention has a similar structure to that of an existing cuff, but a size thereof may be smaller.

The cuff 11 may be formed of various materials. For example, the cuff may be formed of one or an alloy of two or more selected from silicon, gold, silver, iridium, iridium oxide, platinum, tin, nickel, chromium, rhenium, and copper, or a semiconductor device or a metal, which may be implemented as a nano device through a nano process.

The nanowire module 20 includes a plurality of nanowires. In other words, a plurality of nanowires 21 are collected to form a nanowire module 20.

As shown in FIG. 13, the nanowires 21 are arranged in a long line in a longitudinal direction on the inner side of the cuff 11 to form a nanowire module in a line form. However, the array or disposition of the nanowires 21 is not limited to the array shown in FIG. 13, and may be disposed in various forms.

As known in FIG. 13, the nanowire 21 is fixed on inner side of the cuff 11 at one lengthwise end thereof to extend vertically.

Thus, a nanowire 21-based probe is disposed on the inner wall of the cuff 11, and the array and number of the probe may be controlled if necessary.

The processing module 40 serves to control nerve signals or electrical stimuli transmitted and received through the nanowires 21.

The processing module 40 is disposed at a position corresponding to the nanowire module 20 on the outer side of the cuff 11, in which one nanowire module 20 may be electrically connected to a plurality of processing modules 40. Further, a plurality of processing modules 40 are electrically connected to each other so that electrical signals or electrical stimuli may be transmitted and received, even when a portion of nerve is cut.

While not shown in the drawings, the processing module 40 may include an internal communication module 511 which transmits and receives data with the external communication module 700.

As shown in the drawings, the support layer 23 may be formed only on the nanowire module 20, but may be formed so as to have the same area as the cuff 11.

Figure 14:
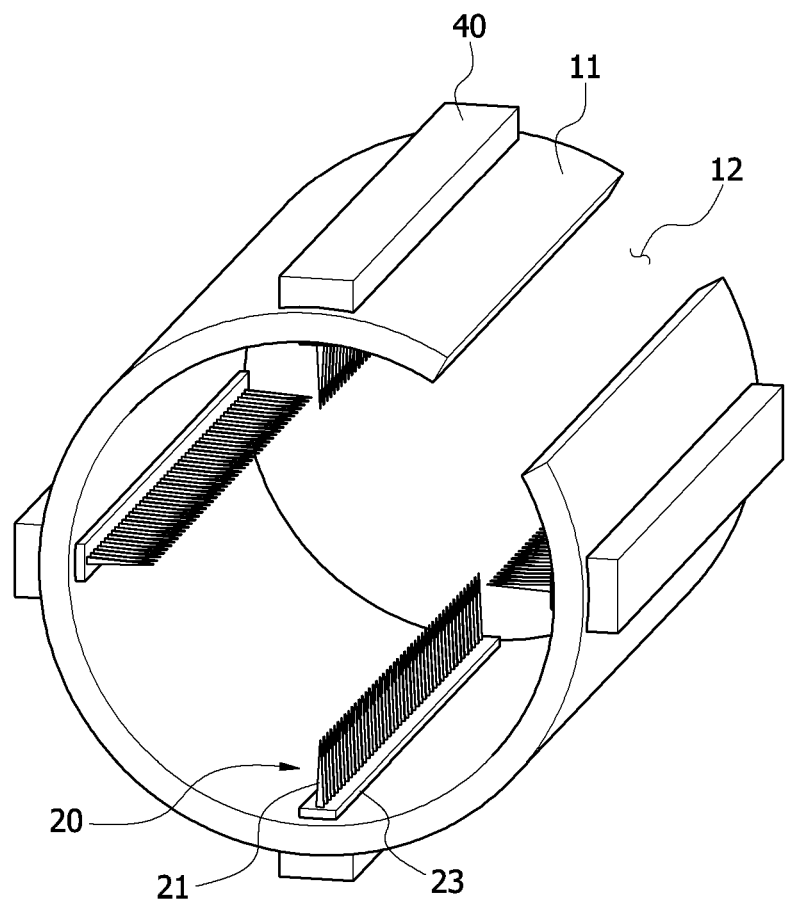

FIG. 14 is a perspective view of a neural device including nanowire modules in a cross form, in which the neural device includes nanowire modules 20 in a cross form.

As shown in FIG. 14, four nanowire modules 20 are disposed so as to face each other in cross form on the inner side of the cuff 11, and are attached at a position corresponding to the nanowire module 20 on the external periphery of the cuff 11.

The nerve fibers forming a nerve bundle transmit nerve signals so as to have different functions, and signals by nerve stimuli are applied or detected in several portions as in a cross form, in which the function of a cuff may be maximized through local stimulation or detection.

Figure 15:
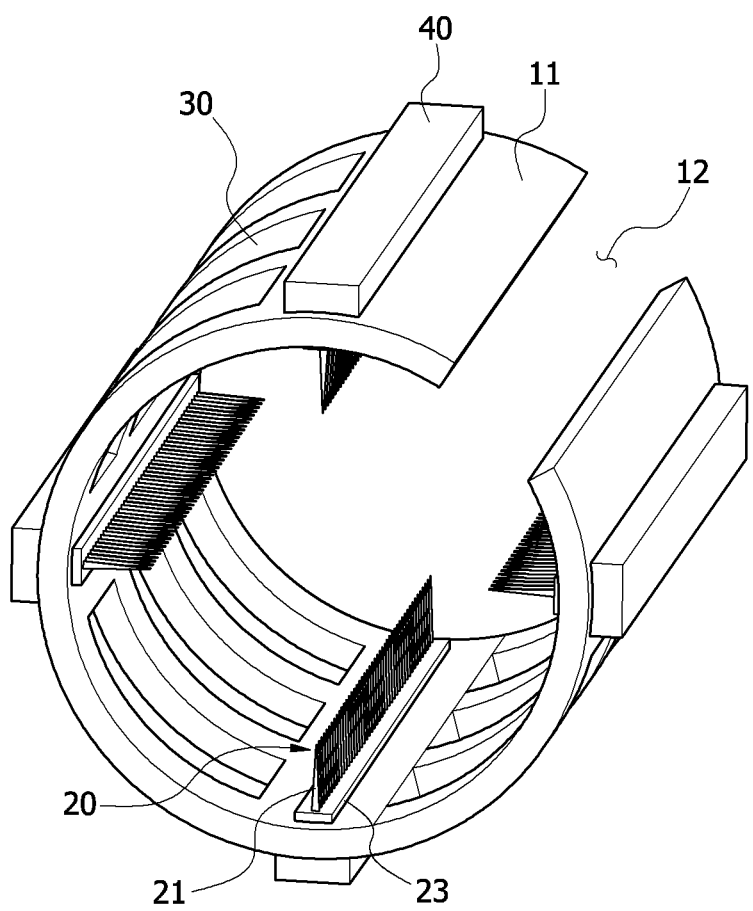

FIG. 15 is a perspective view of a neural device in which the cuff forms a hole for another function, and in which the neural device includes a plurality of holes 30 unlike a neural device of FIGS. 13 and 14.

The holes 30 may have another additional function, for example, a passage for drug transfer from the outside, or the like.

As shown in FIG. 15, the holes 30 may be formed at predetermined intervals in a circumferential direction and a longitudinal direction, but are not limited thereto, and the holes may be disposed in various forms. However, the holes 30 are preferably disposed between the nanowire modules 20 not to be overlapped by or close to the nanowire modules 20.

Figure 16:
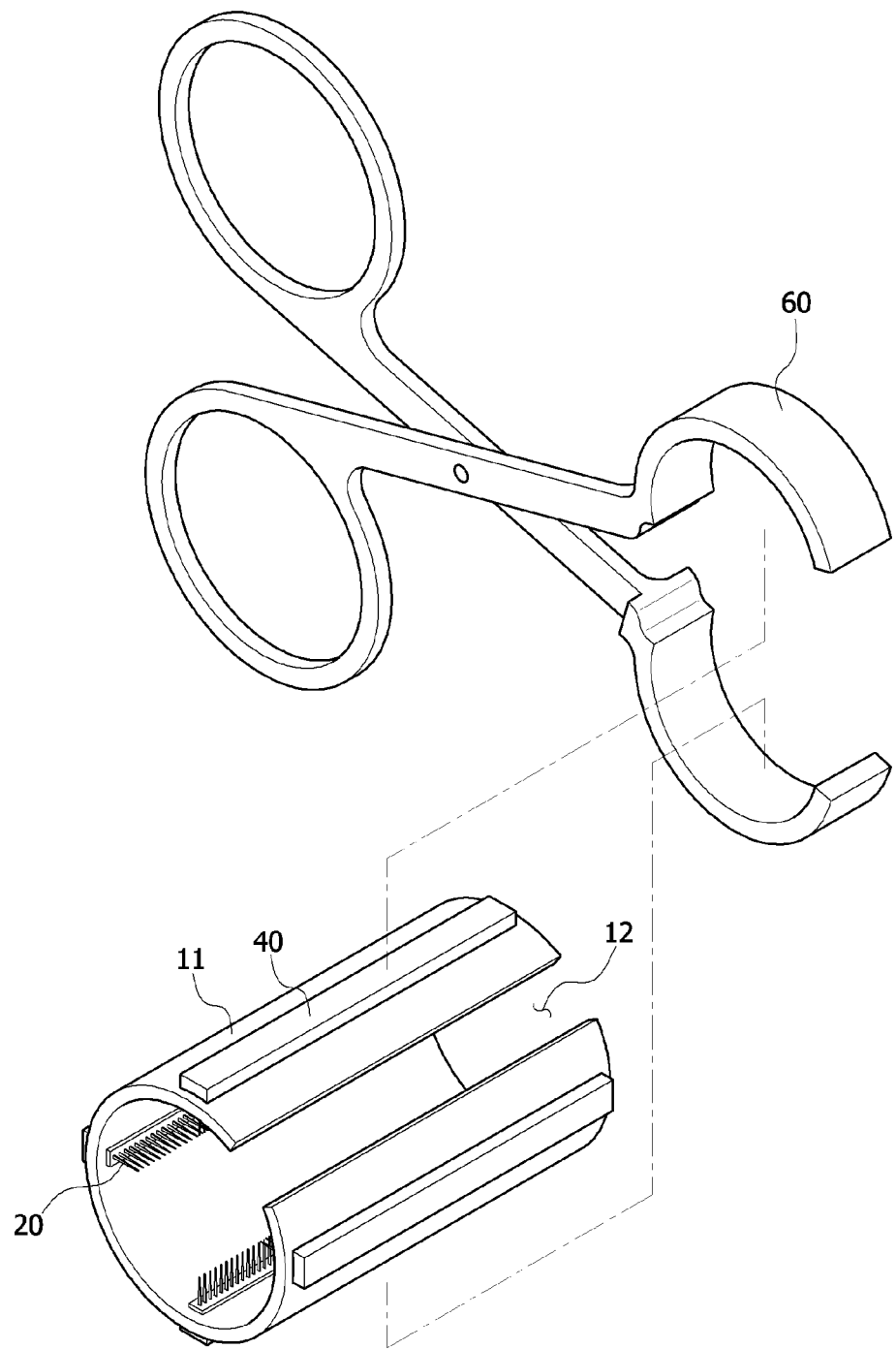

FIG. 16 shows one example of a neural device according to the fourth embodiment of the present invention into which nerves are to be inserted.

First, an open part 12 of a cuff 11 is slightly opened such that nerves 50 can be easily inserted thereinto. At this time, as shown in FIG. 16, the open part of the cuff may be opened using a tightenable surgical tool 60 with a type of tongs. Since the cuff 11 is formed of a cylindrical form, has the open part 12 and is elastic, the cuff may be transformed while maintaining a cylindrical form.

Subsequently, the cuff 11 is inserted so as to surround the nerves 50, and then tightened using the surgical tool 60 to come in contact with the nerves 50.

Thus, since the nerves 50 are inserted into the cuff 11 through the open part 12, there is no damage to nerves by insertion into the cuff 11.

The neural device according to the fourth embodiment of the present invention is capable of transmitting and receiving electrical signals or electrical stimuli by electrically connecting a plurality of processing modules to each other even when a portion of nerve is cut. Further, since a size thereof may be varied, a specific nerve bundle may be selected for stimulation or signal detection. Further, since a cuff structure surrounding nerves is selected, there is no damage to the nerves.

The description of FIGS. 11 and 12 also applies to the neural device according to the fourth embodiment of the present invention.

Figure 17:
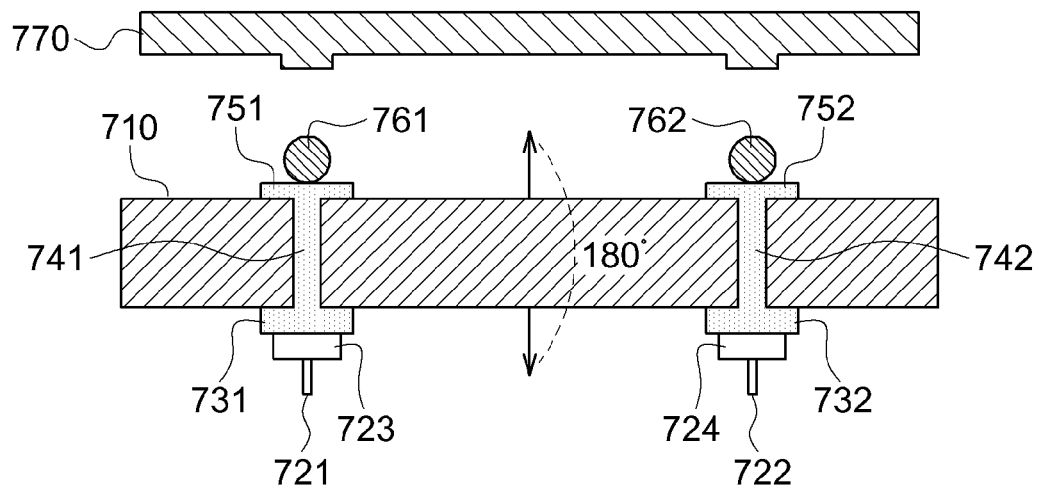
FIGS. 17 to 20 show a neural device according to a fifth embodiment of the present invention.

FIG. 17 shows one example of a neural device according to a fifth embodiment of the present invention. The neural device according to this embodiment includes a substrate 710 or a cuff, nanowires 721 and 722, support layers 723 and 724, electrodes 731 and 732, via holes 741 and 742, electrode pads 751 and 752, and touch balls 761 and 762.

The electrodes 731 and 732 of each of the nanowires 721 and 722 are connected through the via holes 741 and 742 to the electrode pads 751 and 752 of the opposite surface of the substrate, respectively. In other words, the electrode 731 of the nanowire 721 is connected through the via hole 741 to the electrode pad 751 and the electrode 732 of the nanowire 722 is connected through the via hole 742 to the electrode pad 752.

The electrode pad 751 outputs electrical signals obtained from the nerve fibers through the nanowire 721 or applies signals for electrical stimuli to the nanowire 721. The electrode pad 752 outputs electrical signals obtained from the nerve fibers through the nanowire 722 or applies signals for electrical stimuli to the nanowire 722.

The electrode pad 751 is connected to the processing module 770 through the touch ball 761 and the electrode pad 752 is connected to the processing module 770 through the touch ball 762.

Thus, the nanowire, and the electrode pad and the processing module disposed at opposite surfaces of the substrate are electrically connected to each other using a via hole technique. Since the surface of the substrate on which the nanowire is installed is opposite to the surface of the substrate on which the electrode pad and the processing module are installed, an angle between normal vectors thereof is about 180°.

While not shown in FIG. 17, the substrate may include a CMOS region. The CMOS region is a region on the substrate used to implement a CMOS device. The via holes 741 and 742 may be preferably disposed so as to avoid CMOS regions.

Further, while not shown in FIG. 17, bases may be installed at the electrodes 731 and 732 to position the nanowires.

The base may include at least one through hole. The through hole may have various cross-sections such as a circular shape, an oval shape, a polygonal shape, etc, and in particular, a circular shape, which can be easily manufactured, or a shape corresponding to a cross-section of a nerve bundle. In this case, the through-hole may have a diameter of tens of micrometers to tens of nanometers.

In particular, the through-hole formed in the base may be connected to a via hole formed in the substrate. In this case, the nerve fiber may be recovered through the through-hole or the via hole.

In addition, the base may be provided with a nanowire support frame configured to support the nanowire. In this case, the nanowire support frame may be installed at an inner periphery of the through-hole. The nanowire support frame supports the nanowire such that the nanowire can be fixed in one direction. That is, the nanowire is fixed by the nanowire support frame The nanowire support frame may be configured to divide the through-hole into a plurality of regions. The nanowire support frame may have a straight shape or a curved shape having various radii of curvature. In addition, the nanowire support frame may extend from the inner periphery of the through-hole or extend from any one surface of the base.

Figure 18:
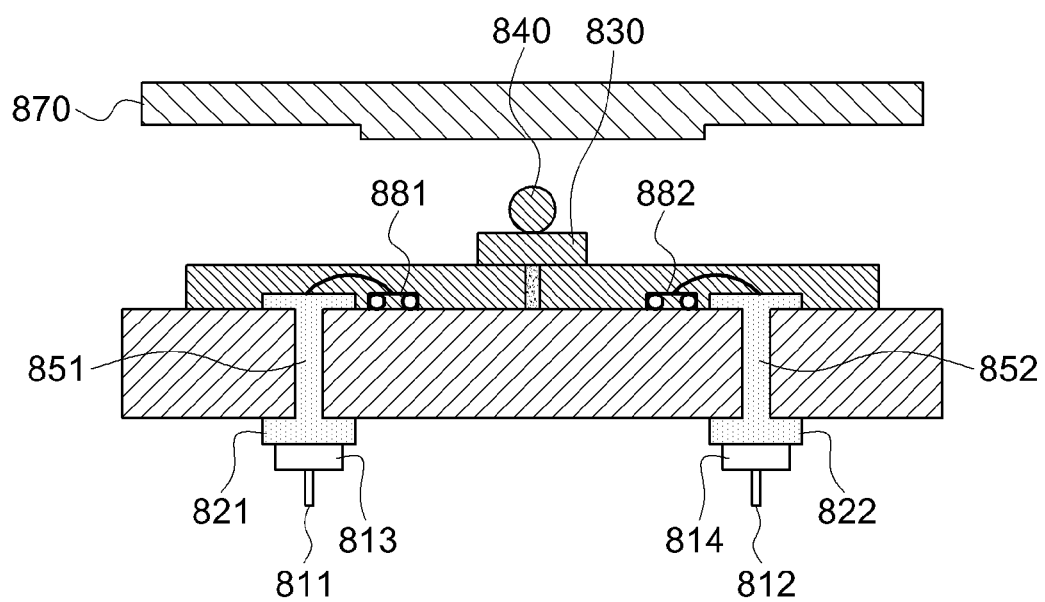

FIG. 18 is similar to FIG. 17, but underscores that a nanowire probe is connected to a gate or a drain of CMOS.

Referring to FIG. 18, the neural device according to this embodiment includes nanowires 811 and 812, support layers 813 and 814, electrodes 821 and 822, via holes 851 and 852, CMOS devices 881 and 882, an electrode pad 830, and a touch ball 840.

In an example shown in FIG. 18, one electrode pad 830 and one touch ball 840 are shown, but at least two electrode pads and touch balls are included depending on number of the nanowires 811 and 812.

The electrodes 821 and 822 of each of the nanowires 811 and 812 are connected through the via holes 851 and 852 at the opposite surface of the substrate, respectively. In this case, the nanowires 811 and 812 are connected to a drain or a gate of the CMOS devices 881 and 882, respectively.

The electrode pad 830 outputs electrical signals obtained from the nerve fibers through the nanowires 811 and 812 or applies signals for electrical stimuli to the nanowires 811 and 812.

The electrode pad 830 is connected to the processing module 870 through the touch ball 840.

Thus, the nanowire, and the electrode pad and the processing module disposed at opposite surfaces of the substrate are electrically connected to each other using a via hole technique. Since the surface of the substrate on which the nanowire is installed is opposite to the surface of the substrate on which the electrode pad and the processing module are installed, an angle between normal vectors thereof is about 180°.

Figure 19:
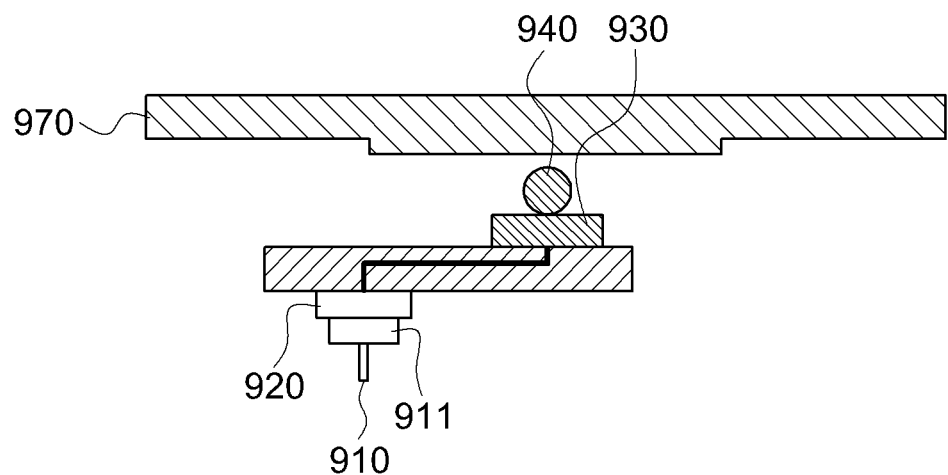

FIG. 19 is a drawing showing a nanowire probe device. The nanowire probe device according to this embodiment includes a nanowire 910, a support layer 911, an electrode 920, an electrode pad 930, and a touch ball 940.

The touch ball 940 is electrically connected to a processing module 970 connected to a device. The nanowire 910 is formed at a surface of a base opposite to the touch ball 940, and provides an electrical signal measured from a nerve fiber to the device through the touch ball 940 or applies an electrical stimulus from the device to the nerve fiber on the basis of a signal applied through the touch ball 940.

The nanowire 910 is connected to the touch ball 940 through the electrode 920 and the electrode pad 930.

The embodiment shown in FIG. 19 corresponds to a case in which only the nanowire probe device in contact with the substrate through the touch ball 940 is separated. That is, the embodiment shown in FIG. 19 shows a method of connecting a nanowire probe end made using a via hole, independently from the device, to the device using the touch ball. The technical sprit of the present invention includes both of a case in which the nanowire and a contact pad are connected to each other using the via hole of the substrate (included in a device), and a case in which the probe device in which the nanowire and the contact pad connected to the touch ball are disposed at opposite surfaces is electrically connected to the substrate using the touch ball (independently configured from the device)

Figure 20:
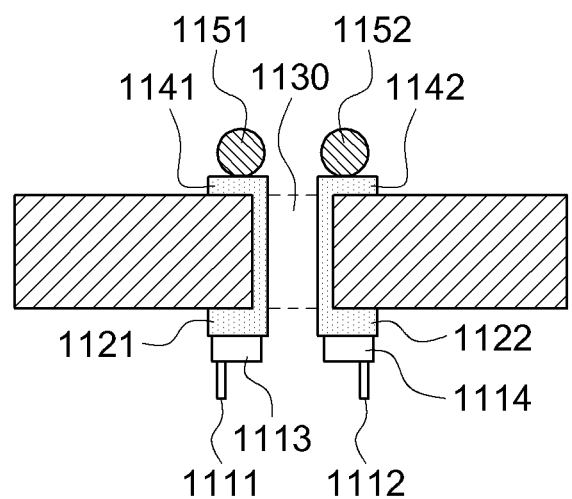

FIG. 20 is a drawing showing another example of connection between an electrode and a pad, which are disposed at opposite surfaces of a substrate, through a via hole.

Referring to FIG. 20, electrodes 1121 and 1122, on which nanowires 1111 and 1112 and support layers 1113 and 1114 are formed, are connected to electrode pads 1141 and 1142 through a via hole 1130, respectively. That is, the electrode 1121 is connected to the electrode pad 1141, and the electrode 1122 is connected to the electrode pad 1142.

A touch ball 1151 is formed on the electrode pad 1141, and a touch ball 1152 is formed on the electrode pad 1142.

In the example shown in FIG. 20, connection between the electrodes 1121 and 1122 and the electrode pads 1141 and 1142 is performed by a portion of the via hole 1130, and the remaining portion of the via hole 1130 remains intact. That is, the via hole 1130 need not be entirely filled with a metal. Only a partial space may be filled with a metal, the electrodes on both surfaces of a substrate may be connected to each other, and the remaining portion may remain as a space. In this case, an outer surface of the remaining hole portion may be coated. Further, a nerve fiber, a neural tissue, or the like may be generated through the remaining hole portion.

In addition, a through hole formed in a base may be connected to a via hole formed in the substrate. In this case, the nerve fiber may be recovered through the through hole or the via hole, and a space in the via hole may be effectively used to recover the nerve fiber or the neural tissue as the space is increased.

Further, in the neural device according to the fifth embodiment of the present invention, nanowires are formed in a different direction from a processing module and thereby cannot be disturbed when being inserted into nerves.

While not shown in the drawings, the processing modules 770, 870, and 970 according to the fifth embodiment may include an internal communication module 511 which transmits and receives data with the external communication module 700.

It is clear to those skilled in the art that the prevent invention may be implemented to other embodiments without departing from the spirit and scope of the invention. Therefore, it should be understood that the above-mentioned description are not construed to restrictive, but are exemplary in all aspects. The scope of the invention is determined only by rational interpretation of the appended claims and various modifications may be made to the described embodiments as defined in the appended claims and their equivalents.

The invention claimed is:

1. A neural device comprising:
   a substrate,
   at least one nanowire which is fixed on the substrate at a lengthwise end thereof and inserted into nerves to obtain electrical signals from nerve fibers or apply electrical signals to the nerve fibers; and
   at least one support layer which is formed on the substrate and which surrounds and supports at least one portion of the nanowire,
   wherein a plurality of nanowires are configured to form a plurality of nanowire modules,
   wherein the neural device comprises a processing module which is electrically connected to the plurality of nanowire modules and which transmits and receives electrical signals or electrical stimuli between nanowire modules selected from the plurality of nanowire modules,
   wherein the nanowire modules are formed on a first surface of a substrate, and the processing module is formed on a second surface of the substrate different from the first surface,
   wherein an angle between a normal vector of the second surface and a normal vector of the first surface is 170° to 180°, and the nanowire module and the processing module are connected to each other through a via hole.

2. The neural device of claim 1, wherein the support layer includes at least one material selected from the group consisting of an insulating material, a biocompatible material, and a biodegradable material.

3. The neural device of claim 1, wherein the support layer includes a drug.

4. The neural device of claim 1, wherein the processing module processes electrical signals obtained from a nanowire module selected from the plurality of nanowire modules, and applies electrical stimuli to another nanowire module.

5. The neural device of claim 1, wherein the substrate is a patch type flexible substrate.

6. The neural device of claim 1, wherein the nanowire modules are disposed in a lattice form.

7. The neural device of claim 1, wherein holes are formed in the substrate.

8. The neural device of claim 7, wherein the holes are disposed in a lattice form.

9. The neural device of claim 1, wherein the via hole is disposed outside of a complementary metal oxide semiconductor (CMOS) region of the substrate.

10. The neural device of claim 1, wherein the processing module includes an internal communication module to transmit and receive data with an external communication module installed externally.

11. The neural device of claim 10, wherein the internal communication module and the external communication module transmit and receive data by radio frequency (RF) or a wire.

12. The neural device of claim 11, wherein the data includes electrical signals obtained from nerve fibers or electrical stimuli applied to the nerve fibers.

13. A neural device comprising:
  a cuff formed in hollow cylindrical form and having an open part in which a portion of a cylindrical periphery is cut;
  a plurality of nanowire modules including at least one nanowire which is fixed on the inner side of the cuff at a lengthwise end thereof and which is inserted into nerves to obtain electrical signals from nerve fibers or apply electrical signals to nerve fibers;
  at least one support layer which is formed on the inner side of the cuff and which surrounds and supports at least one portion of the nanowire; and
  a processing module which is electrically connected to the plurality of nanowire modules and transmits and receives electrical signals or electrical stimuli between nanowire modules selected from the plurality of nanowire modules,
  wherein the nanowire module is formed on a first surface of the cuff, and the processing module is formed on a second surface of the cuff different from the first surface,
  wherein an angle between a normal vector of the second surface and a normal vector of the first surface is 170° to 180°, and the nanowire module and the processing module are connected to each other by a via hole.

14. The neural device of claim 13, wherein the support layer includes a drug.

15. The neural device of claim 13, wherein the processing module processes electrical signals obtained from a nanowire module selected from the plurality of nanowire modules, and applies electrical stimuli to another nanowire module.

16. The neural device of claim 13, wherein the nanowires are arranged in one direction to form a nanowire module in a line form.

17. The neural device of claim 13, wherein the nanowire modules are disposed so as to face each other in a cross form.

18. The neural device of claim 13, wherein a hole is formed in the cuff.

19. The neural device of claim 13, wherein the via hole is disposed outside of a complementary metal oxide semiconductor (CMOS) region of the cuff.

20. The neural device of claim 13, wherein the processing module includes an internal communication module to transmit and receive data with an external communication module installed externally.

21. The neural device of claim 20, wherein the internal communication module and the external communication module transmit and receive data by radio frequency (RF) or a wire.

22. The neural device of claim 20, wherein the data includes electrical signals obtained from nerve fibers or electrical stimuli applied to the nerve fibers.

* * * * *